United States Patent
Larsson et al.

(10) Patent No.: US 11,656,216 B2
(45) Date of Patent: May 23, 2023

(54) MONITORING PROCESS FOR A GREASE LUBRICATED ROTATING SYSTEM AND CORRESPONDING SYSTEM

(71) Applicant: Aktiebolaget SKF, Gothenburg (SE)

(72) Inventors: Per-Erik Larsson, Lulea (SE); Fredrik Sundquist, Luleå (SE)

(73) Assignee: Aktiebolaget SKF, Gothenburg (SE)

( * ) Notice: Subject to any disclaimer, the term of this patent is extended or adjusted under 35 U.S.C. 154(b) by 46 days.

(21) Appl. No.: 17/365,031

(22) Filed: Jul. 1, 2021

(65) Prior Publication Data

US 2022/0011289 A1    Jan. 13, 2022

(30) Foreign Application Priority Data

Jul. 13, 2020 (DE) .......................... 102020208701.6

(51) Int. Cl.
    *G01N 33/28*    (2006.01)
    *G01N 27/04*    (2006.01)
    *G08B 21/18*    (2006.01)

(52) U.S. Cl.
    CPC ....... *G01N 33/2847* (2013.01); *G01N 27/048* (2013.01); *G01N 33/2888* (2013.01); *G08B 21/182* (2013.01)

(58) Field of Classification Search
    CPC ............. G01N 33/2847; G01N 27/048; G01N 33/2888; G08B 21/182
    USPC ....................................................... 340/660
    See application file for complete search history.

(56) References Cited

U.S. PATENT DOCUMENTS

| 4,471,444 | A | * | 9/1984 | Yee ..................... G05B 19/4065 |
|           |   |   |        | 73/104 |
| 5,656,767 | A | * | 8/1997 | Garvey, III ........ G01N 33/2888 |
|           |   |   |        | 324/324 |
| 6,196,057 | B1 | * | 3/2001 | Discenzo .............. F16C 33/667 |
|           |   |   |        | 73/54.01 |
| 9,341,612 | B2 | * | 5/2016 | Gorritxategi .......... G01N 21/85 |
| 9,995,344 | B2 | * | 6/2018 | Dittes ................ G01N 33/2847 |
| 2016/0069856 | A1 | * | 3/2016 | Gorritxategi .......... G01N 21/85 |
|           |   |   |        | 356/70 |
| 2017/0159716 | A1 | * | 6/2017 | Dittes .................... F16J 15/324 |
| 2018/0158261 | A1 | * | 6/2018 | Ottikkutti .......... G01N 33/2888 |
| 2018/0238851 | A1 | * | 8/2018 | Sundquist ............. G01M 13/04 |
| 2018/0299375 | A1 | * | 10/2018 | Young .................... G01N 21/94 |
| 2021/0262894 | A1 | * | 8/2021 | Saarinen ............... G01M 13/04 |
| 2021/0396731 | A1 | * | 12/2021 | Ahmed ................ G01N 1/2035 |
| 2022/0229113 | A1 | * | 7/2022 | Maki ...................... H02H 5/041 |
| 2022/0252482 | A1 | * | 8/2022 | Hashizume ............. F16C 41/00 |

* cited by examiner

*Primary Examiner* — Zhen Y Wu
(74) *Attorney, Agent, or Firm* — Garcia-Zamor Intellectual Property Law, LLC; Ruy Garcia-Zamor

(57) ABSTRACT

A monitoring process for a grease lubricated rotating system having a processing unit linked to a measurement system for measuring the water content within lubrication grease. A learning period is performed that establishes upper and lower thresholds based on current measurements. If at least a first number of measurements out a second number of last measurements are above the upper threshold then if such is the case, emitting a first event. If at least the first number of measurements out the second number of last measurements are below the lower threshold, then if such is the case, emitting a second event, if at least a first event has been emitted, if such is the case emitting an alarm function of the at least first event.

9 Claims, 1 Drawing Sheet

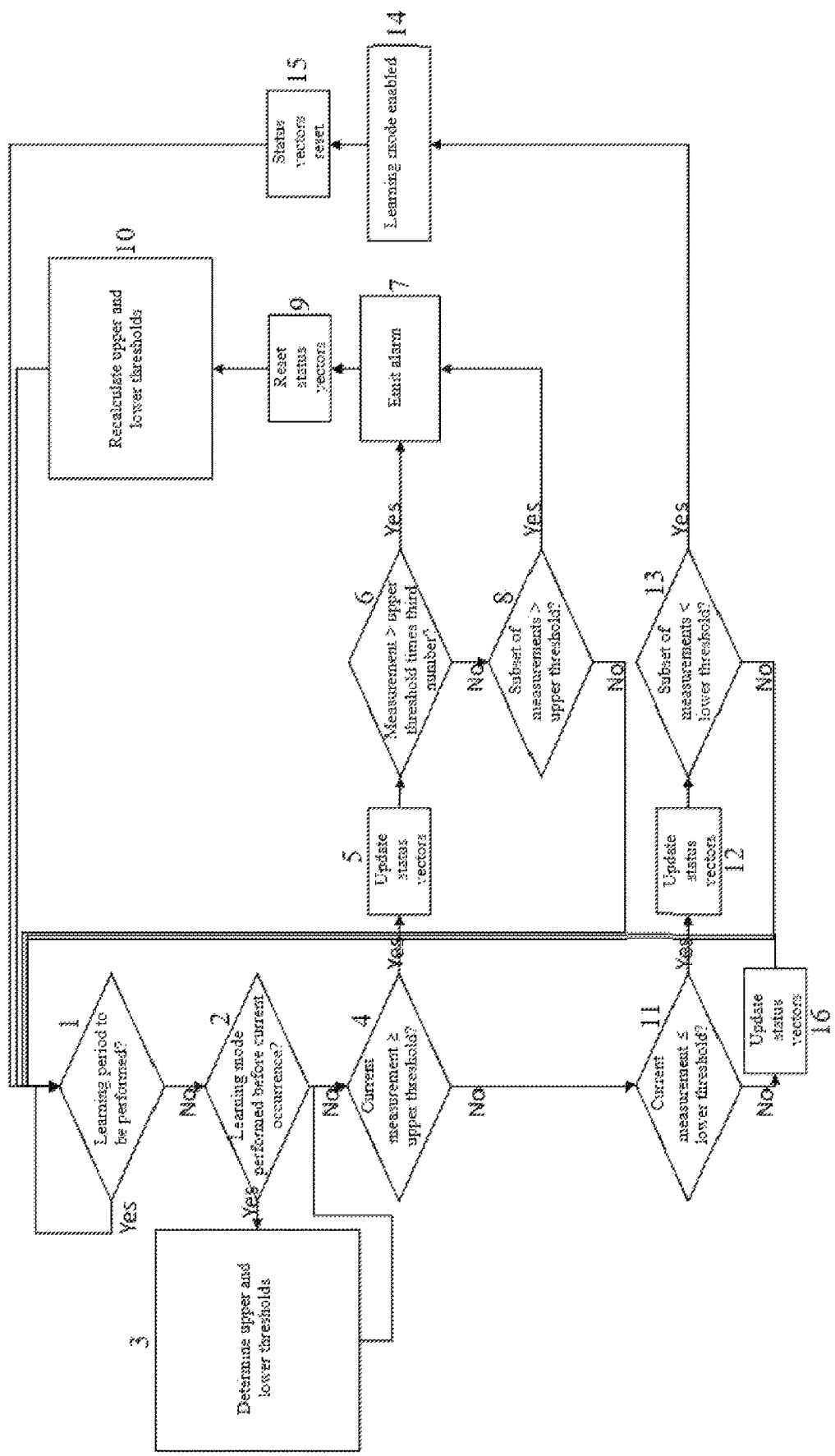

MONITORING PROCESS FOR A GREASE LUBRICATED ROTATING SYSTEM AND CORRESPONDING SYSTEM

CROSS-REFERENCE TO RELATED APPLICATIONS

This application claims priority to German Patent Application no. 102020208701.6, filed Jul. 13, 2020, the contents of which is fully incorporated herein by reference.

TECHNICAL FIELD OF THE INVENTION

The present invention relates to bearings lubrication, and particularly to water content measurement within bearing grease.

BACKGROUND OF THE INVENTION

Rotating systems require lubrication in order to maintain reliable operation conditions. Such a lubrication is generally achieved using oil or grease. However, grease is generally preferred for lubrication of closed systems, such as bearings.

The grease is contained using housings and seals. Seal failure generally leads to entry of dust and/or water. A low concentration of water within the grease is acceptable. However, it exists a threshold above which the presence of water within grease decreases the lubrication of the rotating system and can lead to damage or destruction.

Monitoring systems allow to determine the water content within grease so that corrective measures can be taken before the above-mentioned threshold is crossed.

Document US-2018-238851 discloses such a monitoring system comprising an electrode in contact with the grease to monitor, and connected to a resistor R in order to form a RC circuit.

A change of water content in the grease is detected as the impedance of the RC circuit changes due to a change of the dielectric contestant of mixture of grease and water.

The existing monitoring systems involve random sampling of grease for offline analysis and manual adjustment to alarms and sensor detection thresholds based on the offline analysis results.

The present monitoring system alleviates the need for any sampling or threshold setting.

SUMMARY OF THE INVENTION

An object of the invention is a monitoring process for a grease lubricated rotating system comprising a processing unit linked to a measurement system for measuring the water content within lubrication grease, comprising the following steps:

determining if a learning period is to be performed during which measurements are recorded for a predetermined period and if such is the case, determining an upper threshold and a lower threshold based on the mean value and the standard deviation of the water content within grease measurements recorded during the learning period, then, for each measurement, determining if the current measurement is greater than or equal to the upper threshold, and when such is the case, determining if at least a first number of measurements out a second number of last measurements are above the upper threshold then if such is the case, emitting a first event, determining if a current measurement is smaller or equal to the lower threshold, and when such is the case, determining if at least the first number of measurements out the second number of last measurements are below the lower threshold, then if such is the case, emitting a second event, determining if at least a first event has been emitted, if such is the case emitting an alarm function of the at least first event.

An upper threshold status vector and a lower threshold status vector can be 1-dimensional vectors with a length equal to the second number, comprising recordings of the comparison results of up to the second number of last measurements with, respectively the upper threshold and the lower threshold, each vector being initialized by being filled with a first value.

The status vectors can be updated by shifting the current values within each status vector by one value thereby deleting the last of the current values, and by inserting a value at the beginning each status vector, a second value being inserted in the upper threshold status vector and the first value in the lower threshold status vector after it is determined the current measurement is greater than or equal to the upper threshold, the first value being inserted in the upper threshold status vector and the second value in the lower threshold status vector after it is determined the current measurement is lower than or equal to the lower threshold, the first value being inserted in the upper threshold status vector and in the lower threshold status vector after it is determined the current measurement is greater than the lower threshold and lower than the upper threshold, and the upper threshold status vector and the lower threshold status vector can be reset by filling with first values after it is determined that at least the first number of measurements out of the second number of last measurements are below the lower threshold.

It can be determined if the current measurement is greater than or equal to a third number times the upper threshold, if such is the case, emitting a first event.

New upper threshold and lower threshold can be determined out of a preset number of measurements right after the first event is emitted.

A new learning period can be triggered each time either a first event or a second event occurs.

The rotating system can be a bearing.

The steps of determining if at least a first event has been emitted, if such is the case emitting an alarm function of the at least first event, can be realized before a new learning period, after a new learning period, in the background, or in parallel to the other steps.

Another object of the invention is a monitoring system for a grease lubricated rotating system comprising a processing unit linked to an measurement system for measuring the water content within lubrication grease, the processing unit being configured for executing the steps comprised in the monitoring process as described above.

The measurement system can comprise an electrode in contact with the grease connected in serial with a current source and a resistor and measurement means connected in parallel with the resistor, the output signal of the electrolytic measurement system being linked to the voltage drop across the resistor.

The monitoring system and process are advantageous because they are simpler and present a lower cost without a need for calibration thanks to the use of a relative method instead of an absolute one.

They also allow for a reduced risk of making configuration errors and allows for automatic recalculation of alarm level when a new baseline is established.

BRIEF DESCRIPTION OF THE DRAWINGS

The present invention will be better understood from studying the detailed description of a number of embodiments considered by way of entirely non-limiting examples and illustrated by the attached drawing in which:

FIG. 1 shows the main steps of a monitoring process according to a first embodiment of the invention.

DETAILED DESCRIPTION OF THE INVENTION

The monitoring system comprises a processing unit linked to a measurement system for measuring the water content within lubrication grease of a rotating system, in particular a bearing. The processing unit comprises typically a processor and at least a memory for storing data.

The electrolytic measurement system comprises an electrode in contact with the grease connected in serial with a current source and a resistor and measurement means connected in parallel with the resistor. The output signal of the electrolytic measurement system is linked to the voltage drop across the resistor.

Instead of trying to achieve absolute measurement of the water content within the grease, the present system seeks to determine relative measurement of the water content in regard of a predetermined period wherein the water content is considered to be low enough to avoid any damage to the machine.

An embodiment of the invention is illustrated by FIG. 1. The process starts by a first step 1 during which it is determined if a learning period is to be performed. If such is the case, measurements are recorded for a predetermined period. If such is not the case, a measurement is recorded for the current occurrence. At step 2, it is determined if the learning mode has been performed immediately before the current occurrence. If such is the case, the process proceeds to a third step 3. If such is not the case, the process proceeds to a step 4.

During the third step 3, an upper threshold TH and a lower threshold TL are determined. The thresholds are functions of the mean value μ and the standard deviation σ of the water content within grease measurements recorded during the predetermined period.

$$TH = \mu + x^{*}\sigma \quad \text{(Eq. 1)}$$

$$TL = y^{*}\mu \quad \text{(Eq. 2)}$$

With $1 < x < 10$ and $0,1 < y < 0,9$

The process then continues at step 4.

If it is determined at step 1 that a learning period is not performed, the process continues directly at step 4.

At a step 4, it is determined if the current measurement is greater than or equal to the upper threshold. If such is the case, the upper threshold status vector and the lower threshold status vector are updated during a step 5. The upper threshold status vector is 1-dimensional vectors with a length equal to N, comprising recordings of the comparison results of up to the last N measurements with the upper threshold TH. The lower threshold status vector is similar in structure, and comprises recordings of the comparison results of up to the last N measurements with the lower threshold TL. Each vector is initialized by being filled with a first value (i.e. 0). See updated flowchart for clarification.

During step 5, the status vectors are updated by shifting the current values within each status vector by one value thereby deleting the last of the current values, and inserting at the beginning of the upper threshold status vector a second value (i.e. 1). and inserting at the beginning of the lower threshold status vector a value equal to the first value.

At a step 6, it is determined if the measurement is above the upper threshold TH times a third number (i.e. 100).

If such is the case, the process proceeds with a step 7 during which an alarm is emitted.

If such is not the case, the process proceeds with a step 8 during which it is determined if at least a number of measurements equal to the first number out of a number of the last measurements equal to the second number are above the upper threshold TH.

If such is the case, the process proceeds to the step 7.

If such is not the case, the process resumes at step 1.

After an alarm is emitted at step 7, the process proceeds with a step 9, during which the status vectors are reset, then, with a step 10, during which the upper threshold TH and the lower threshold TL are recalculated thanks to equations Eq. 1 and Eq. 2 based on the measurements record during a predetermined duration right before the present occurrence. Performing such a recalculation of the threshold saves time equal to the predetermined duration for the learning period. Instead of waiting for the recording needed for the learning period to be gathered, the process determines the new thresholds out of the measurements already recorded. The process then resumes at step 1.

If at step 4, it is determined if the current measurement is lower than the upper threshold, the process proceeds to step 11. During step 11, it is determined if the current measurement is lower than or equal to the lower threshold TL. If such is not the case, the process proceeds with a step 16 during which the status vector is updated. During step 16, the status vectors are updated by shifting the current values within each status vector by one value thereby deleting the last of the current values, and inserting at the beginning of each status vector a value equal to the first value.

The process then resumes at step 1.

If during step 11, it is determined that the current measurement is lower than or equal to the lower threshold TL, the process proceeds with a step 12 during which the status vectors are updated. During step 12, the status vectors are updated by shifting the current values within each status vector by one value thereby deleting the last of the current values, and inserting at the beginning of the upper threshold status vector a value equal to the first value and inserting at the beginning of the lower threshold status vector a value equal to the second value.

The process then proceeds with a step 13 during which it is determined if at least a number of measurements equal to the first number out of a number of last measurements equal to the second number are below the lower threshold TL. If such is not the case, the process resumes at step 1. If such is the case, the process proceeds with a step 14 during which the learning mode is enabled. During a step 15, the status vectors are reset so that only first values are comprised within and the process proceeds with step 1.

In an alternative embodiment, a second number of measurements are kept in memory or are recorded. Steps 5, 12, 14 and 16 are deleted, and alternate steps 8 and 13 comprise determining if at least a number of measurements equal to the first number out of a number of last measurements equal to the second number are respectively, above the upper threshold TH or below the lower threshold TL.

The invention claimed is:

1. A method for monitoring a grease used as a lubricant in a rotating system comprising:

providing an electrode configured to measure the lubricant;

providing a processing unit engaged with the electrode for measuring a water content within the grease;

determining by the processing unit if a learning period will be performed, the learning period comprising a predetermined period of time during which a plurality of measurements of the water content in the grease are recorded, wherein when the learning period is performed by the processing unit, the processing unit determines an upper threshold and a lower threshold based on the mean value and the standard deviation of the plurality of measurements;

determining by the processing unit if a current measurement is greater than or equal to the upper threshold, when the current measurement is greater than or equal to the upper threshold then the processing unit determines a number of subsequent high measurements, the processing unit then compares the number of subsequent high measurements to a first predetermined limit and if the number of subsequent high measurements is greater than the first predetermined limit designating an occurrence of a first event, determining by the processing unit if the current measurement is smaller than or equal to the lower threshold, when the current measurement is smaller than or equal to the lower threshold the processor then determines a number of subsequent low measurements, the processing unit then compares the number of subsequent low measurements to a second predetermined limit and if the number of subsequent low measurements exceeds the second predetermined limit designating the occurrence of a second event, determining if the first event is designated and, if so, emitting a first event alarm function, and determining if the second event is designated and, if so, emitting a second event alarm function.

2. The method of claim 1, wherein an upper threshold status vector and a lower threshold status vector are 1-dimensional vectors with a length equal to a second number, comprising recordings of the comparison results of up to the second number of last measurements with, respectively the upper threshold and the lower threshold, each vector being initialized by being filled with a first value.

3. The method of claim 2, wherein the upper threshold status vector and the lower threshold status vector are updated by shifting the current values within each status vector by one value thereby deleting the last of the current values, and by inserting a value at the beginning each status vector, a second value being inserted in the upper threshold status vector and the first value in the lower threshold status vector after it is determined determining if the current measurement is greater than or equal to the upper threshold, the first value being inserted in the upper threshold status vector and the second value in the lower threshold status vector after it is determined determining if the current measurement is lower than or equal to the lower threshold, the first value being inserted in the upper threshold status vector and in the lower threshold status vector after it is determined determining if the current measurement is greater than the lower threshold and lower than the upper threshold, and the upper threshold status vector and the lower threshold status vector are reset by filling with first values after it is determined that determining if at least the first number of measurements out of the second number of last measurements are below the lower threshold.

4. The method of claim 1, wherein the step of designating the first event further comprises if the current measurement is greater than or equal to a third number times the upper threshold, then the first event is designated.

5. The method of claim 1, wherein a new upper threshold and a new lower threshold are determined out of the preset number of measurements right after the first event alarm function is emitted.

6. The method of claim 1, wherein a new learning period is triggered each time either the first event or the second event occurs.

7. The method of claim 1, wherein the rotating system is a bearing.

8. A monitoring device for a grease used as a lubricant in a rotating system comprising:

an electrode configured to measure the lubricant;

a processing unit engaged with the electrode for measuring a water content within the grease; the processing unit being configured to determine whether a learning period will be performed, the learning period comprising a predetermined period of time during which a plurality of measurements of the water content in the grease are recorded, wherein when a learning period is performed by the processing unit, the processing unit determines an upper threshold and a lower threshold based on the mean value and the standard deviation of the plurality of measurements;

wherein the processing unit is configured to determine if a current measurement is greater than or equal to the upper threshold, when the current measurement is greater than or equal to the upper threshold then the processing unit determines a number of subsequent high measurements, the processing unit then compares the number of subsequent high measurements to a first predetermined limit and if the number of subsequent high measurements is greater than the first predetermined limit designating an occurrence of a first event, wherein the processing unit is configured to determine if the current measurement is smaller than or equal to the lower threshold, when the current measurement is smaller than or equal to the lower threshold the processor then determines a number of subsequent low measurements, the processing unit then compares the number of subsequent low measurements to a second predetermined limit and if the number of subsequent low measurements exceeds the second predetermined limit designating the occurrence of a second event, wherein if the first event is designated, the device emits a first event alarm function, and wherein if the second event is designated, the device emits a second event alarm function.

9. The monitoring device of claim 8, further comprising:

a current source, a resistor, and a sensor connected in parallel with the resistor, wherein the electrode is in contact with the grease and is connected in series with the current source, the resistor, and the resistor, and wherein the output signal of the electrolytic measurement system being linked to the voltage drop across the resistor.

* * * * *